United States Patent [19]

Takayama et al.

[11] Patent Number: 4,992,168
[45] Date of Patent: Feb. 12, 1991

[54] APPARATUS FOR FRACTIONALLY MEASURING POLYMERS

[75] Inventors: Shigeru Takayama; Yukitaka Goto, both of Yokkaichi, Japan

[73] Assignee: Mitsubishi Petrochemical Company Limited, Tokyo, Japan

[21] Appl. No.: 318,243

[22] Filed: Mar. 3, 1989

[30] Foreign Application Priority Data

Mar. 7, 1988 [JP] Japan ................... 63-53236

[51] Int. Cl.$^5$ .............................. B01D 15/08
[52] U.S. Cl. ................... 210/198.2; 210/656; 210/101; 55/386; 73/61.1 C; 422/70
[58] Field of Search ............ 210/635, 656, 198.2, 210/101; 55/386; 73/61.1 C; 422/70

[56] References Cited

FOREIGN PATENT DOCUMENTS 627975 2/1987 Japan ................. 210/198.2

OTHER PUBLICATIONS

U.S. Patent Office translation of Kokai 62-7975 (PTO-4393), Sep. 1990, pp. 1-18.

Primary Examiner—Ernest G. Therkorn
Attorney, Agent, or Firm—Wegner, Cantor, Mueller & Player

[57] ABSTRACT

An apparatus for fractionally measuring a polymer comprising: a flow path change valve unit A having an inlet for pouring a sample polymer solution, a loop for metering the sample polymer solution, an internal standard solution pouring mechanism including a loop for metering the liquid and a valve for pouring the liquid, and a valve for changing the system flow path; a composition fractionation unit B which is provided with a column filled with a filler, and which permits the polymer dissolved in the sample polymer solution transferred from the loop for metering the sample polymer solution to precipitate on the filler, and then fractionally dissolves the polymer by stepwise raising the temperature in the column; a molecular size fractionation unit C which is provided with a column filled with a filler, and which fractionates, depending upon the molecular size, the sample polymer fraction solution which has undergone composition fractionation in the unit B and which is batchwisely transferred therefrom; a solvent feeding unit D which feeds at a predetermined flow rate a solvent for use in the fractional dissolution of the sample polymer in the unit B and for transferring the obtained sample polymer fraction solutions; a detection unit E which deflects the results of fractionation obtained in the unit C and measures the molecular weight distribution; a system controller; and automatic temperature controllers.

6 Claims, 4 Drawing Sheets

APPARATUS FOR FRACTIONALLY MEASURING POLYMERS

BACKGROUND OF THE INVENTION

1. Field of the Art

This invention relates to an apparatus for analyzing the correlation between the molecular weight and the chemical structure or the molecular structure of polymers within short periods of time.

In general, polymers are mixtures in which any one or all of the molecular species such as molecular weight, chemical composition, molecular structure and the like, are nonhomogeneous. The quality of a polymer is usually determined by these molecular species. It is therefore indispensable to obtain proper distribution data concerning these molecular species for studies to improve the quality of polymers.

Gel permeation chromatography (GPC), the fractional precipitation or dissolution method, and other polymer fractionating methods are performed for this purpose. These fractionating methods, however, only give data concerning any one of the above molecular species. If a correlation is found between two or more molecular species, a higher level of molecular design will be possible. For this purpose, it may be suggested to combine two or more fractionating means together. In this case, however, two or more different fractionating methods must be carried out in a two-dimensional manner. That is, a given molecular species is first fractionated, according to a given fractionating method and then the obtained fractions are subjected to other fractionating methods, requiring laborious work and extended periods of time (usually more than one week).

2. Background Art

The so-called column method, which belongs to the category of the fractional dissolution method, has been proposed for determining the distribution of methyl branches (distribution of composition or, in this case, crystallinity distribution) in polyethylene ("Polymer Preprints", Vol. 18 (2), 1977, pp. 182–187). Thus, a polymer solution is passed through a small column filled with an inert filler (chromosorb P) such that the surface of the filler is coated with the polymer. Next, the temperature of the column is continuously raised to elute the polymer in the order of increasing crystallinity or decreasing methyl branches, and the eluates are introduced into a differential refractometer to obtain a distribution curve of methyl branch from the data from the differential refractometer and the column temperature (the number of methyl branches decreases with increase in column temperature). The above literature teaches that the methyl branch distribution (crystallinity distribution) and the molecular weight distribution should preferably be combined together, but does not disclose any specific examples.

On the other hand, the method in which the column is filled with a porous filler and a polymer solution passed therethrough to elute the polymer in the order of decreasing molecular sizes, is called the GPC method and has been widely used for determining the molecular weight distribution of the polymer (Aldgeld et al., "Gel Permeation Chromatography", published by Marcell Decker Co., U.S.A., 1971).

If these two methods are combined together, the correlation can be analyzed between the chemical structure or molecular structure of a polymer and the molecular weight distribution. However, the aforementioned problem with regard to the speed of analysis is not solved even if they are simply combined together, i.e., for example, a polymer is fractionated depending upon the molecular structure using the fractional dissolution column method and then the molecular weight distributions are determined for each of the obtained fractions by the GPC method.

In order to solve the above-mentioned problem, i.e., to carry out two-way fractionation consisting of molecular composition fractionation and molecular size fractionation within short periods of time, the present inventors have already proposed a method in Japanese Patent Publication No. 7975/1987. This method comprises precipitating a polymer to be analyzed on a filler in a column, eluting the precipitated polymer while stepwise raising the temperature, and batchwisely sending the polymer fractions fractionated at each temperature step into a molecular weight distribution analyzer, in effecting composition fractionation by the fractional dissolution column method. The above publication further introduces an apparatus for concretely putting this method into practice. This apparatus comprises a composition fractionation unit A provided with a fractional dissolution column for effecting the stepwise fractional dissolution and a flow path change valve, a molecular size fractionation unit B for fractionating, depending on the molecular size, the polymer that is fractionated by the unit A, a solvent feeding unit C that feeds to the units A and B a solvent for use in the fractional dissolution of the sample polymer and for transferring the polymer solution, and a detection unit D for detecting the results of fractionation obtained in the unit B, and wherein an automatic temperature controller and a valve controller are connected to the unit A.

This apparatus draws attention from the standpoint of effectively putting the above-mentioned method into practice, but is not satisfactory for practical use. For example, the sealing performance of the valves for changing flow path decreases since the valves and the composition fractionation column, which undergoes great temperature change, are accommodated in the same unit. Furthermore, there is no mechanism for confirming the performance of the column and the constant displacement of pumps. This apparatus thus involves serious problems in the lowering of the measuring precision and in the maintenance of the apparatus when the operation is continued for extended periods of time.

SUMMARY OF THE INVENTION

The object of the present invention is to improve the above-mentioned apparatus and to provide an apparatus for fractionally measuring polymers, which possesses improved measuring precision and can be continuously operated for extended periods of time. This object is achieved (1) by establishing independent temperature control systems to meet the characteristics of the individual operation mechanisms, and (2) by providing an internal standard solution pouring mechanism for confirming the performance of the column used, and for confirming the constant displacement of pumps.

Thus, the apparatus for fractionally measuring polymers according to the present invention comprises:
a flow path change valve unit A having an inlet for pouring a sample polymer solution, a loop for metering the sample polymer solution, an internal standard solution pouring mechanism including a loop for metering the standard solution and a valve for pouring the standard solution, and a valve for changing the system flow path;

a composition fractionation unit B which is provided with a column filled with a filler, and which permits the polymer dissolved in the sample polymer solution transferred from said loop for metering the sample polymer solution to precipitate on said filler, and then fractionally dissolves the polymer by stepwisely raising the temperature in said column;

a molecular size fractionation unit C which is provided with a column filled with a filler, and which fractionates, depending upon the molecular size, the sample polymer fraction solution which has undergone composition fractionation in the unit B and which is batchwisely transferred therefrom;

a solvent feeding unit D which feeds at a predetermined flow rate a solvent for use in the fractional dissolution of the sample polymer in the unit B and for transferring the obtained sample polymer fraction solutions;

a detection unit E which detects the results of fractionation obtained in the unit C and measures the molecular weight distribution;

a system controller; and automatic temperature controllers which are connected to the units A, B and C and which independently perform temperature control to ensure free flow of the polymer solution;

wherein said system controller controls said temperature controllers and the valve in said unit A.

According to the apparatus for fractionally measuring the polymer of the present invention, the flow path change valve unit A and the molecular composition fractionation unit B are independent from each other, and the temperatures are independently controlled in the units A, B and C, which improves the maintenance of the apparatus. Moreover, the measuring precision is guaranteed by the introduction of the internal standard solution pouring mechanism. Thus, according to the present invention, the aforementioned problems are overcome, and fully-automatic two-way fractionation and measurement concerning the molecular composition and molecular size of a polymer on the practical level is successfully carried out in an in-line manner.

unit A—flow path change valve unit
unit B—composition fractionation unit
unit C—molecular size fractionation unit
unit D—solvent feeding unit
unit E—detection unit
Aa, Ba, Ca—automatic temperature controllers
Ab—system controller
j—sample polymer metering loop
k—composition fractionation column
n—internal standard solution tank
q—internal standard solution metering loop
$s_1, s_2$—GPC columns

DETAILED DESCRIPTION OF THE INVENTION

1. System for fractional measurement

Figure 1:
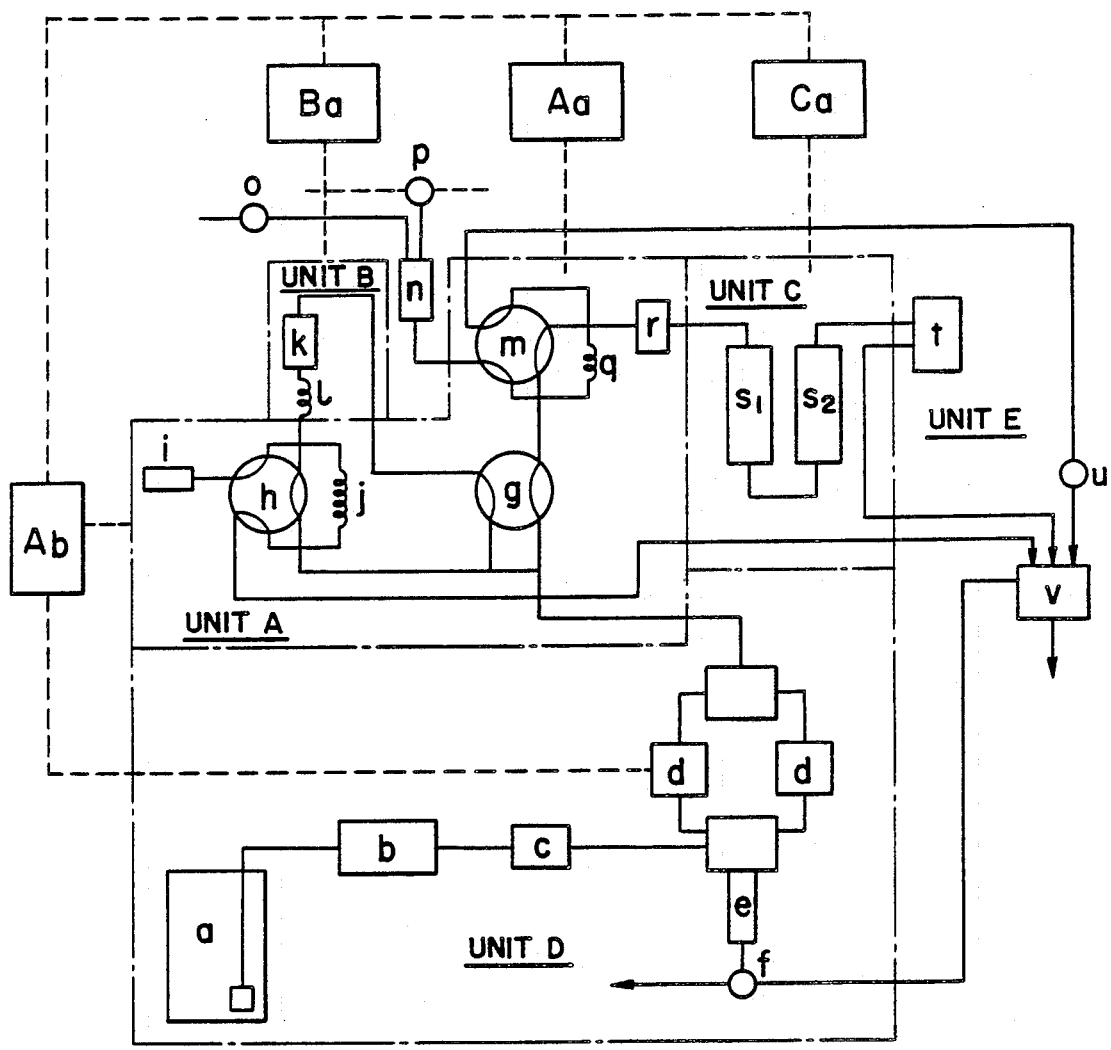
FIG. 1 is a system diagram illustrating an embodiment of the apparatus for fractionally measuring polymers according to the present invention.
Figure 2A:
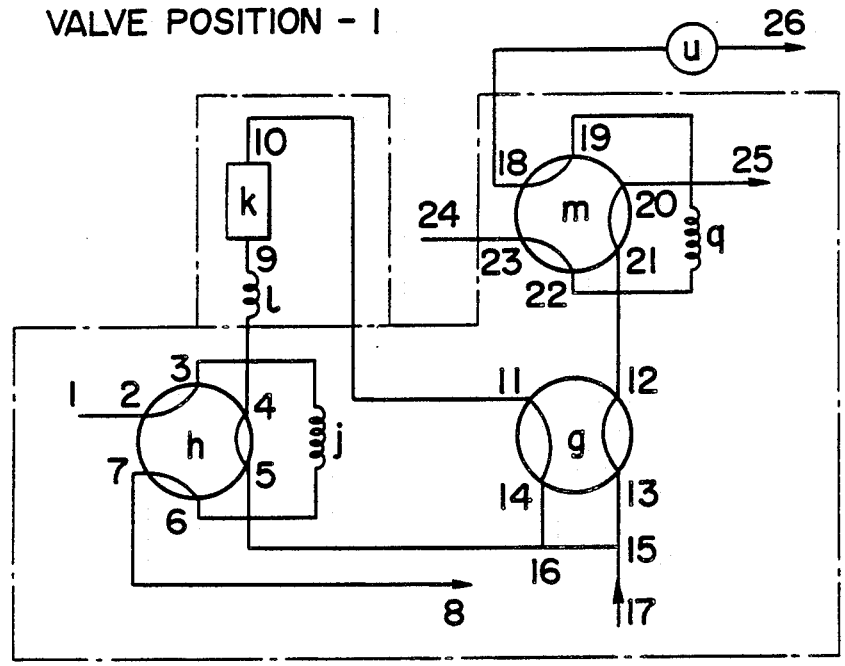
FIG. 2 is a piping diagram showing the positions of valves in the flow path change valve unit A. In the drawings.
Figure 2B:
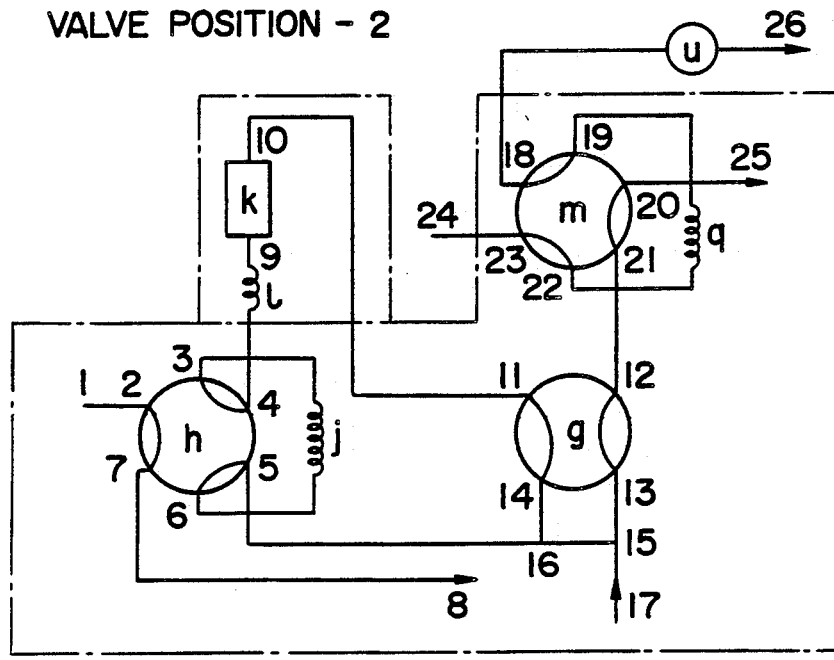
Figure 2C:
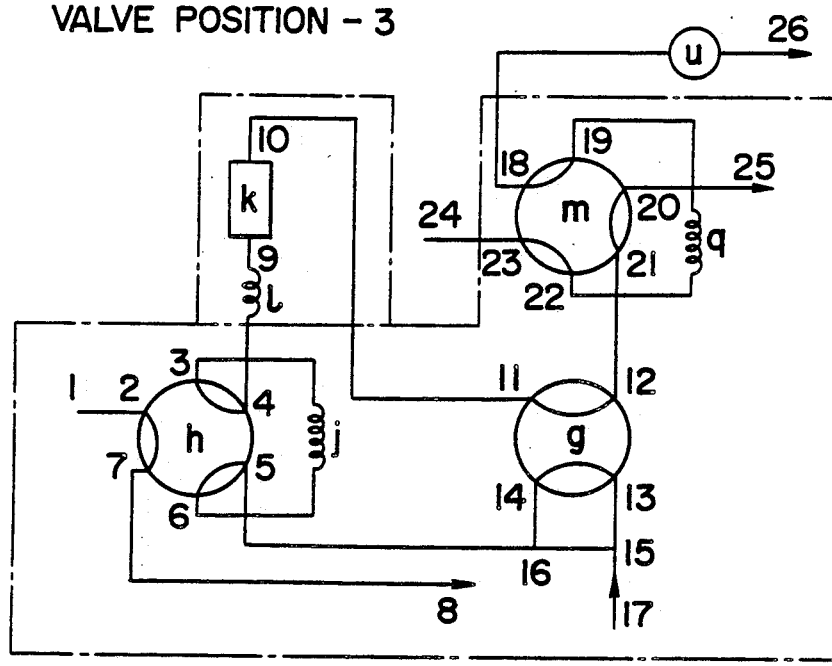
Figure 2D:
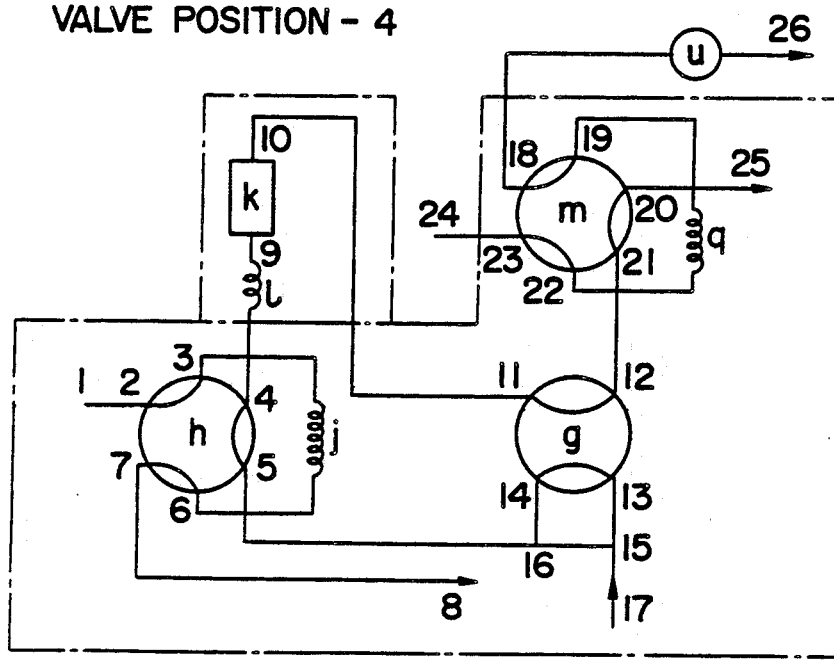
Figure 2E:
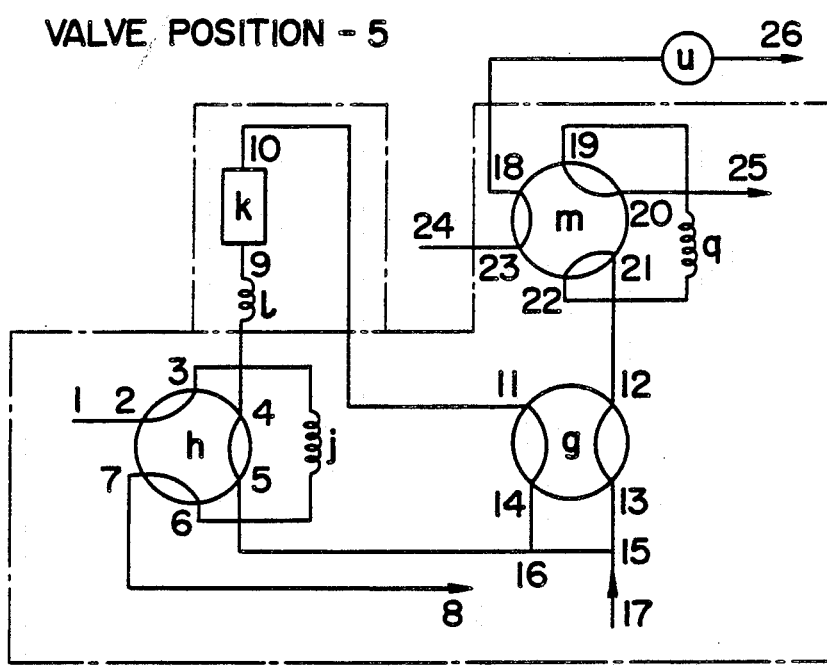

FIG. 1 is a system diagram illustrating an embodiment of the apparatus for fractionally measuring polymers according to the present invention.

A unit A is a heating container, i.e., an oven having valves for changing the flow path of the system. A sample polymer solution or a fractionated polymer solution passes through the valves in the oven. Therefore, the valves are maintained at a predetermined temperature at which the polymer solution is allowed to flow freely.

The valves are switched by a system controller Ab which works to control the whole apparatus.

A unit B is a composition fractionation unit which works utilizing the temperature dependency of the solubility of the sample polymer to the solvent. Unit B is also contained in a heating container, i.e., in an oven. The fractionation is carried out by stepwisely raising the temperature of the polymer that is once precipitated. The temperature must then be lowered for the next fractionation. Therefore, unit B is provided with an automatic temperature controller Ba which works to raise or lower the temperature in synchronization with system controller Ab.

A unit C is a molecular size fractionation unit which fractionates, depending upon the molecular size, the polymer which has been fractionated depending upon the composition. Unit C is also contained in a heating container, i.e., in an oven.

A unit D is a unit for feeding at predetermined flow rates a solvent for use in the fractional dissolution of the sample polymer in unit B and for transferring the polymer solution.

A unit E is a detection unit for detecting the results of fractionation obtained in unit C. A flow cell of the detector is maintained at a predetermined temperature at which the polymer solution is allowed to flow freely. The detected result is recorded on a recorder or on a data processor.

Ovens of units A, B and C are maintained at temperatures that permit the polymer solution to pass freely through. To meet particular functions and operability, however, the temperatures are controlled independently. For this purpose, automatic temperature controllers Aa, Ba and Ca are therefore connected to the ovens of units A, B and C, respectively. The polymer is guaranteed to flow freely even when units A and B have the same temperature. In unit B, however, the temperature changes repeatedly at all times. If the valves are provided in the oven in which the temperature changes as mentioned above, the valve sealing deteriorates due to the temperature change and the operation cannot be continued for extended periods of time. Moreover, oven C which effects the fractionation depending upon the molecular size must be maintained at a constant temperature at all times for maintaining the life of the fractionation column and for maintaining the precision for measuring the molecular size. Therefore, oven C should not be installed in the neighborhood of the oven (unit B) in which the temperature changes. Units A and C are maintained at predetermined temperatures. For reasons of easiness in replacing the filter (r) and repairing the valves in unit A, however, unit A must be independent from unit C in which the temperature cannot change suddenly.

In FIG. 1 is shown a basic flow path which, however, may be modified to some extent depending upon the types of detectors and so on.

| Symbol | Content |
| --- | --- |
| a: | Solvent tank |
| b: | Pre-pump |
| c: | Filter |
| d: | Pump head (fixed displacement pump) |
| e: | De-airing tube |
| f: | Three-way valve |
| g: | Injection valve |
| h: | Sample valve |
| i: | Sample inlet |
| j: | Sample loop (metering loop) |
| k: | Fractionation column (crystallinity) |
| l: | Pre-heating loop |
| m: | Internal standard solution pouring valve |
| n: | Internal standard solution tank |
| o: | Internal standard solution pouring valve |
| p: | Three-way valve |
| q: | Internal standard solution metering loop |
| r: | Filter |
| $s_1, s_2$: | GPC columns |
| t: | Detector |
| u: | Internal standard solution outlet valve |
| v: | Waste liquor tank |

2. Fractionating operation

The valves in unit A are set to valve position -1, and a sample polymer solution is poured from inlet i using an injector or the like. A loop j is filled with the solution supplied from the inlet i via valve ports 2 and 3. An excess of solution is drained from 8 passing through valve ports 6 and 7.

After the loop is filled with the polymer solution, the valves change automatically to valve positions -2, 3, 4, 1 by the instruction of the system controller unit Ab, and all or part of the solution in the loop is introduced into a composition fractionation column k. The solution is transferred into the column in valve position -3 through the conduit route 6-3-4-9 while being extruded by the solvent that is supplied from unit D through the conduit route 17-15-16-5.

After the solution of a predetermined amount is introduced into column k, the valves change to valve position -4 (the amount of solution introduced is determined by the flow rate of the fixed displacement pump and the setpoint time at valve position -3, however, the maximum amount is determined by the metering loop j).

Thereafter, the solution moves until it is set to the center of column k and is stopped as the valves change to valve position -1 (this timing is set by the flow rate of the fixed displacement pump, the inner volume of the conduit portion of 4 through up to 9, and the inner volume of column k).

Next, unit B is cooled to a temperature sufficient for most of the polymer dissolved in the solution in column k to precipitate and form a thin film on the surfaces of the filler in the column. The solvent in column k thermally shrinks due to cooling. However, the thermal shrinkage of the solvent is compensated since the solvent is always introduced from unit D to both sides of the column through the by-pass conduit via 15 and 16. If the thermal shrinkage of the solvent at the time of cooling is not compensated, there may occur gas intrusion into (or generation in) column k; i.e., there develops a portion in which the solvent does not flow when the polymer is eluted and whereby the precision of fractionation is deteriorated. Furthermore, when the gas that has intruded (or generated) is sent to the column for effecting molecular size fractionation, the precision of fractionation decreases. This further becomes a cause of noise for the detector.

When a predetermined period of time passes after the column has cooled to a predetermined temperature, the valves automatically change to valve position -4, and the whole amount of the solution containing the non-precipitated polymer only in column k is transferred to unit C through the conduit route 10-11-12-21-20-25 by the solvent of a predetermined volume (from unit D through the conduit route 17-15-16-5-4-9) that flows at a speed which does not disturb the interior of the column. Thereafter, the valves automatically return to valve position -1.

The polymer thus transferred to unit C is a polymer which is soluble at the temperature of unit B. The polymer is fractionated depending upon the molecular size in column S in unit C, and detectors t (differential refractometer, infrared spectrophotometer, and the like) detect the polymer concentration in the solution, the special chemical structure (e.g., carbonyl group, methyl group) of the polymer and the like.

While fractionation is executed in unit C, the temperature of unit B is raised to a predetermined temperature and composition fractionation is carried out at that temperature. The valves automatically change again to valve position -4 after a predetermined period of time has passed during which the fractionation of the polymer solution that is introduced previously into unit C is substantially completed, and the entire amount of the solution containing polymer fraction newly eluted at the above temperature in unit B is transferred to unit C by the solvent of a predetermined volume. The polymer solution thus transferred to unit C is subjected to molecular size fractionation in the same manner as the preceding fractionation.

Valve m and loop q in unit A are mechanisms for pouring an internal standard substance into unit C. The object of pouring the internal standard substance is (1) to confirm the constant displacement of the pump and (2) to confirm the performance of columns k and s. The internal standard substance should be one which is soluble in the solvent at room temperature and can be detected by detector t. In general, use is made of a low molecular weight substance that does not have molecular weight distribution and that does not impair the fractional measurement. The internal standard substance can also be added to the sample polymer solution at inlet i. The internal standard substance is soluble at the first eluting temperature. Therefore, when the soluble polymer in column k is transferred to unit C, the whole amount of the internal standard substance is also transferred from column k. There is thus no internal standard substance in the elution of the second and subsequent times; i.e., the solution of only the polymer is transferred to unit C. In view of this, the following operation is carried out in order to supply the internal standard substance to unit C after the first elution.

Thus, when the whole amount of the polymer solution passes through valve m after the elution operation of the second and subsequent times, valve m automatically changes to be in valve position -5, and the solution containing the internal standard substance in loop q is transferred to unit C. After transference in a predetermined quantiy, the valve automatically returns to valve position -1. Thereafter, a valve U is opened and the internal standard solution in a tank n is introduced into loop q due to $N_2$ pressure applied to tank n. After the time required for substituting the whole amount in loop q has passed, valve u is closed and the operation is finished.

This operation is repeated automatically after the first elution in column k. A valve p attached to the tank is used for pressurizing the tank and for releasing the pressure. The pressure in the tank is controlled by a constant-pressure valve. A valve o is attached to an inlet to charge the internal standard solution into tank n. The first substitution of the internal standard substance in loop q is conducted according to the aforementioned operation after the first elution in column k.

In the subsequent operations, as in the same manner as described above, the temperature of unit B is stepwisely raised to a predetermined value previously programed, and a solution containing a polymer fraction newly eluted at each step is batchwisely transferred to unit C and is fractionated depending upon the molecular size, thereby to carry out the two-way fractionation according to the composition and the molecular weight of the sample polymer.

3. Embodiment of fractional measurement

Principal points of an embodiment of fractional measurement using the apparatus of the invention will now be described below. Needless to say, any suitable modification may be made to specific conditions as set forth below.

(1) Fractionation column k

This column usually has a length of about 5 to 20 cm and an inner diameter of about 1.0 to 0.2 cm, and is preferably made of stainless steel.

The filler should preferably be an inert material such as Celite (diatomaceous earth) or glass beads having a particle size of about 50 to 400 mesh (tyler). Joint portions at the inlet and outlet of the column should preferably be provided with a sintered metallic filter having pores of about 5 to 10μ or with a stainless steel filter having a filter pore size of about 400 mesh (tyler).

To maximize the effect of fractionation, the column should have a space volume of about 0.5 to 2 ml after it is filled with the filler.

(2) Sample solution to be poured

The concentration is about 2 to 20 mg/ml, and is preferably about 10 mg/ml.

The pouring amount is usually about 0.5 to 2 ml (about 1 to 40 mg in terms of polymer weight).

(3) Metering loop j

The inner volume is usually about 0.2 to 2 ml, and is preferably about 1 ml.

(4) Cooling rate of unit B

The cooling rate is usually from 1° to 20° C./min. (i.e., 60° to 1200° C./hour) and is preferably about 2° C./min.

Usually, the cooling rate should not be constant; i.e., the cooling rate should be large at high temperatures and small at low temperatures.

(5) Speed for extruding the solution in fractionation column n

Usually about 0.5 to 2 ml/min. and preferably about 1 ml/min.

(6) Extruded volume of solution in fractionation column k

Usually about 0.5 to 3 ml, and preferably about 1 ml. The volume to be extruded should be determined so that the polymer eluted in the column is extruded in all amounts.

(7) Rate of temperature rise of fractionation column n

Usually about 0.5° to 5° C./min. and preferably about 1° C./min.

(8) Conduit material

A stainless steel is preferably used.

(9) Unit C

The column S has a length of about 30 to 90 cm and an inner diameter of about 4 to 8 mm, and the filler is preferably a crosslinked polystyrene or an inorganic material such as a porous silica, or the like. The number of columns need not necessarily be limited to two, but may be determined according to the range for measuring the molecular weight distribution and the isolation performance.

(10) Detectors

Detectors include a differential refractometer, an infrared spectrophotometer, a viscometer, and the like. Two or more detectors may be used in combination.

For instance, the outlet of the column may be provided with a differential refractometer or an infrared spectrophotometer to measure the polymer concentration in the solvent that flows out, in order to plot the amount of polymer that flows out with the lapse of the time.

(11) Solvent

The solvent should preferably be one for which the index of refraction changes depending upon the change in the polymer concentration, and which exhibits little absorption in the infrared ray region for detection.

Specific examples include o-dichlorobenzene, trichlorobenzene, BTx, carbon tetrachloride, ethylene tetrachloride, and the like.

(12) Internal standard solution metering loop (q)

This loop usually has an inner volume of about 0.2 to 2 ml, and preferably about 1 ml.

(13) Internal standard solution tank (n)

This tank usually has an inner volume of 300 to 500 ml. To prevent the compressed $N_2$ from intruding into the flow path for analysis, a liquid level detector is provided and a mechanism is further provided to stop the internal standard substance solution from being poured when the liquid level becomes lower than the lower limit level.

A specific example of the internal standard substance is a 2,4-t-butyl-p-cresol, which is dissolved in a solvent such as o-dichlorobenzene or the like.

What is claimed is:

1. An apparatus for fractionally measuring a polymer comprising:
   a flow path change valve unit A having an inlet for pouring a sample polymer solution, a loop for metering the sample polymer solution, an internal standard solution pouring mechanism including a loop for metering the standard solution and a valve for pouring the standard solution, and a valve for changing the system flow path;
   a composition fractionation unit B which is provided with a column filled with a filler, and which permits the polymer dissolved in the sample polymer solution transferred from said loop for metering the sample polymer solution to precipitate on said filler, and then fractionally dissolves the polymer by stepwisely raising the temperature in said column;
   a molecular size fractionation unit C which is provided with a column filled with a filler, and which fractionates, depending upon the molecular size, the sample polymer fraction solution which has undergone composition fractionation in the unit B and which is batchwisely transferred therefrom;

a solvent feeding unit D which feeds at a predetermined flow rate a solvent for use in the fractional dissolution of the sample polymer in the unit B and for transferring the obtained sample polymer fraction solutions;

a detection unit E which detects the results of fractionation obtained in the unit C and measures the molecular weight distribution;

a system controller; and automatic temperature controllers which are connected to the units A, B and C and which independently perform temperature control to ensure free flow of the polymer solution;

wherein said system controller controls said temperature controllers and the valve in said unit A.

2. The apparatus for fractionally measuring a polymer according to claim 1, wherein the column filled with the filler in the unit B has a length of 5 to 20 cm and an inner diameter of 1.0 to 0.2 cm.

3. The apparatus for fractionally measuring a polymer according to claim 1, wherein the filler in the column of the unit B is diatomaceous earth or glass beads having a particle size of 50 to 400 mesh (tyler).

4. The apparatus for fractionally measuring a polymer according to claim 1, wherein the column filled with the filler in the unit C has a length of 30 to 90 cm and an inner diameter of 4 to 8 mm.

5. The apparatus for fractionally measuring a polymer according to claim 1, wherein the filler in the column of the unit C is a crosslinked polystyrene or a porous silica.

6. The apparatus for fractionally measuring a polymer according to claim 1, wherein the detection unit E comprises an infrared spectrophotometer.

* * * * *